(12) United States Patent
Tillotson (10) Patent No.: US 9,308,113 B2
(45) Date of Patent: Apr. 12, 2016

(54) DETACHABLE ORTHOPEDIC SLING

(71) Applicant: Charles Douglas Tillotson, Denton, TX (US)

(72) Inventor: Charles Douglas Tillotson, Denton, TX (US)

(*) Notice: Subject to any disclaimer, the term of this patent is extended or adjusted under 35 U.S.C. 154(b) by 341 days.

(21) Appl. No.: 13/862,908

(22) Filed: Apr. 15, 2013

(65) Prior Publication Data

US 2014/0309573 A1 Oct. 16, 2014

(51) Int. Cl.
*A61F 5/00* (2006.01)
*A61F 5/048* (2006.01)
*A61H 1/02* (2006.01)

(52) U.S. Cl.
CPC .............. *A61F 5/048* (2013.01); *A61H 1/0292* (2013.01); *A61H 2201/1284* (2013.01); *A61H 2201/168* (2013.01); *A61H 2201/1614* (2013.01)

(58) Field of Classification Search
CPC ....... A61F 5/042; A61F 5/048; A61H 1/0292; A61H 2201/1284; A61H 2201/1614; A61H 2201/168
USPC ............................ 602/32–36, 37–40; 428/121
See application file for complete search history.

(56) References Cited

U.S. PATENT DOCUMENTS

| 1,116,773 | A | 11/1914 | West et al. |
|---|---|---|---|
| 3,827,429 | A | 8/1974 | Heikes |
| 4,269,179 | A | 5/1981 | Burton et al. |
| 4,396,012 | A | 8/1983 | Cobiski |
| 4,569,340 | A | 2/1986 | Burton |
| 4,991,572 | A | 2/1991 | Chases |
| 5,033,460 | A | 7/1991 | Goldish |
| 5,242,380 | A | 9/1993 | Steinbrueck |
| 5,375,279 | A | 12/1994 | Toso |
| 5,788,659 | A * | 8/1998 | Haas .................. A61F 5/04 602/20 |
| 6,113,564 | A | 9/2000 | McGuire |
| 6,517,506 | B1 | 2/2003 | Pettibon |
| 6,705,974 | B1 * | 3/2004 | Tardif ............... A63B 21/068 482/148 |
| 7,255,666 | B2 | 8/2007 | Cardenas |
| 7,862,526 | B1 | 1/2011 | Skowron et al. |
| 9,061,176 | B2 * | 6/2015 | Nikkaran .......... A63B 21/068 |
| 2013/0345032 | A1 * | 12/2013 | Aldridge ........... A61H 1/0237 482/131 |

OTHER PUBLICATIONS

International Search Report and Written Opinion in Appl. No. PCT/US2014/033562 dated Sep. 9, 2014.
International Preliminary Report on Patentability and Written Opinion dated Oct. 20, 2015.

\* cited by examiner

*Primary Examiner* — Kim M Lewis
(74) *Attorney, Agent, or Firm* — Carter Scholer Arnett Hamada & Mockler, PLLC (57) ABSTRACT

A detachable orthopedic sling for treatment of a user's spine is provided. The detachable orthopedic sling includes first and second adjustable sections, first and second handholds, and a strap. The first and second adjustable sections permit adjustment of their respective lengths. The first and second adjustable sections extend from one or more attachment rings to the first and second handholds. The strap permits adjustment of its length and may be positioned by a user around his torso, under his arms, and across his back. The detachable orthopedic sling may be mechanically coupled to a support structure using the attachment rings and allows the user to hang from the sling to provide traction treatment of the user's spine.

16 Claims, 10 Drawing Sheets

DETACHABLE ORTHOPEDIC SLING

TECHNICAL FIELD OF THE INVENTION

The present application relates generally to therapeutic orthopedic devices and, more specifically, to a detachable orthopedic sling.

BACKGROUND OF THE INVENTION

Back pain is a common and debilitating ailment. Traction is an alternative to surgery, drug therapy, and chiropractic manipulation for treatment of back pain. Some mechanisms for traction therapy require permanent installation in a building or a large, sturdy framework. Such mechanisms may be costly, not portable, and/or not suitable for home use.

SUMMARY OF THE INVENTION

Various embodiments include a detachable orthopedic sling for treatment of a user's spine. In one embodiment, a detachable orthopedic sling includes first and second adjustable sections, first and second handholds, and a strap. The first and second adjustable sections are configured to permit adjustment of their respective lengths. The first and second adjustable sections extend from one or more attachment rings to the first and second handholds. The strap is configured to permit adjustment of its length and to be positioned by a user around his torso, under his arms, and across his back. The detachable orthopedic sling is configured to mechanically couple to a support structure using the one or more attachment rings and to allow the user to hang from the sling to provide traction treatment of the user's spine.

In another embodiment, a detachable orthopedic sling includes a first attachment section, first and second adjustable sections, first and second handholds, and a strap. The first attachment section includes first and second attachment rings. The first and second adjustable sections are permanently coupled to the first and second attachment rings, respectively. The first and second adjustable sections are configured to permit adjustment of their respective lengths. The first and second adjustable sections extend from the first and second attachment rings to the first and second handholds, respectively. The strap is configured to permit adjustment of its length and to be positioned by a user around his torso, under his arms, and across his back. The detachable orthopedic sling is configured to mechanically couple to a support structure using the one or more attachment rings and to allow the user to hang from the sling to provide traction treatment of the user's spine.

Other technical features may be readily apparent to one skilled in the art from the following figures, descriptions and claims.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 10, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged method and apparatus for payment of invoices.

The present disclosure relates to a detachable sling for therapeutic treatment of a human spine. The sling may be temporarily attached to a structure for use in providing therapeutic traction treatment of a user's spine. When not in use, the sling may be detached from the structure for storage, transportation, or other purpose. Examples of structures to which the sling may be temporarily attached include, but are not limited to, a door of a building or vehicle, a tree branch or other horizontal bar, or a body of a truck or other vehicle.

Figure 1:
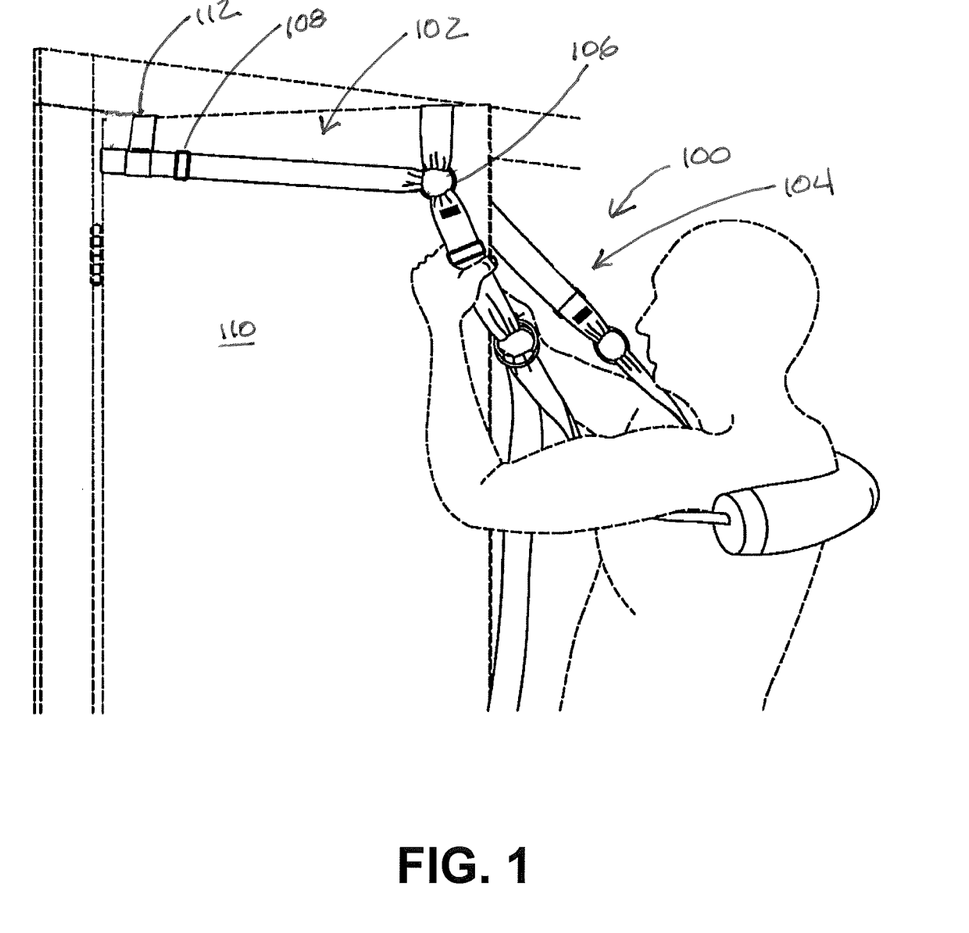
FIG. 1 presents an orthogonal view of a detachable orthopedic sling according to an exemplary embodiment of the disclosure.
Figure 2:
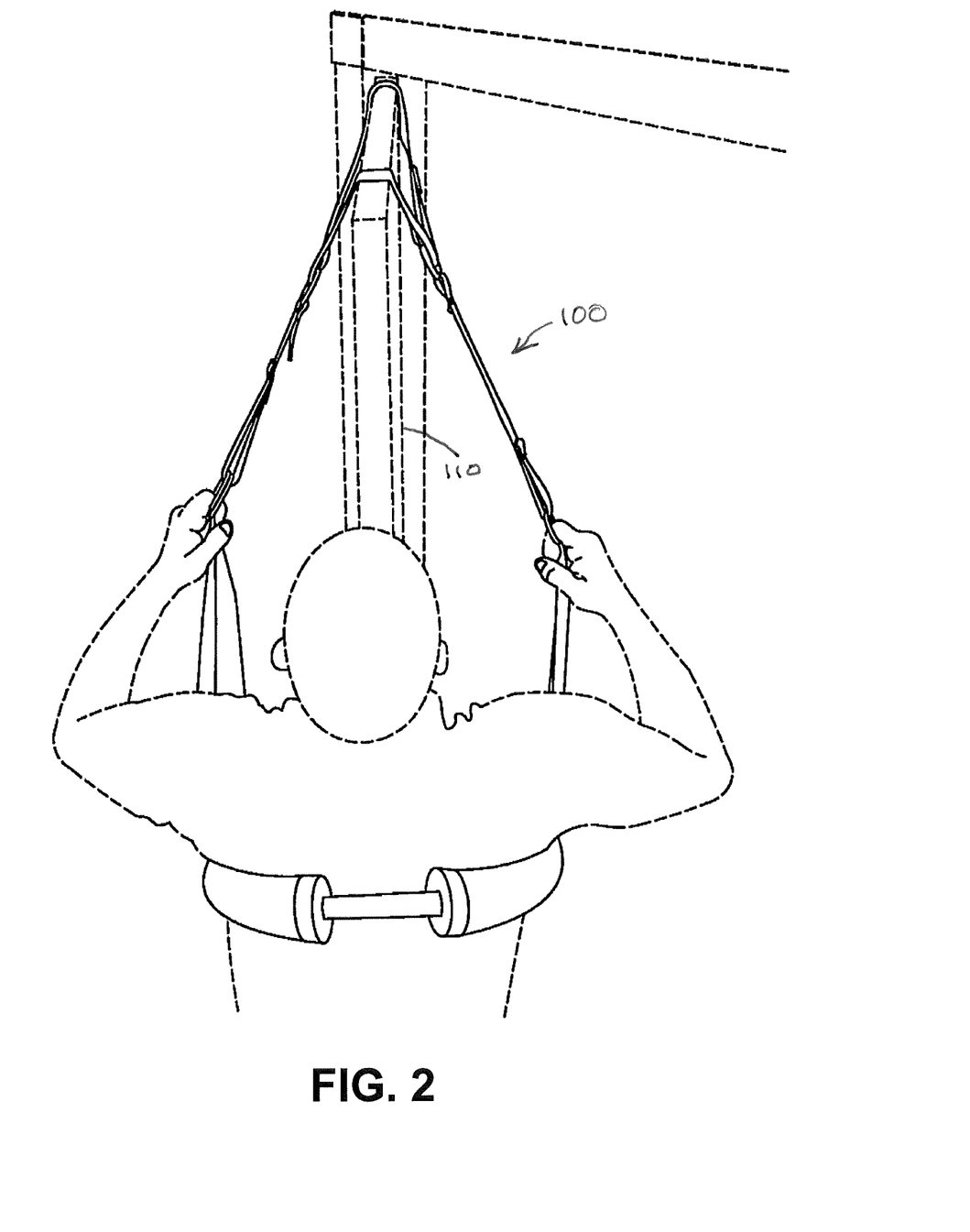
FIG. 2 presents a second orthogonal view of a detachable orthopedic sling according to an exemplary embodiment of the disclosure.
Figure 3:
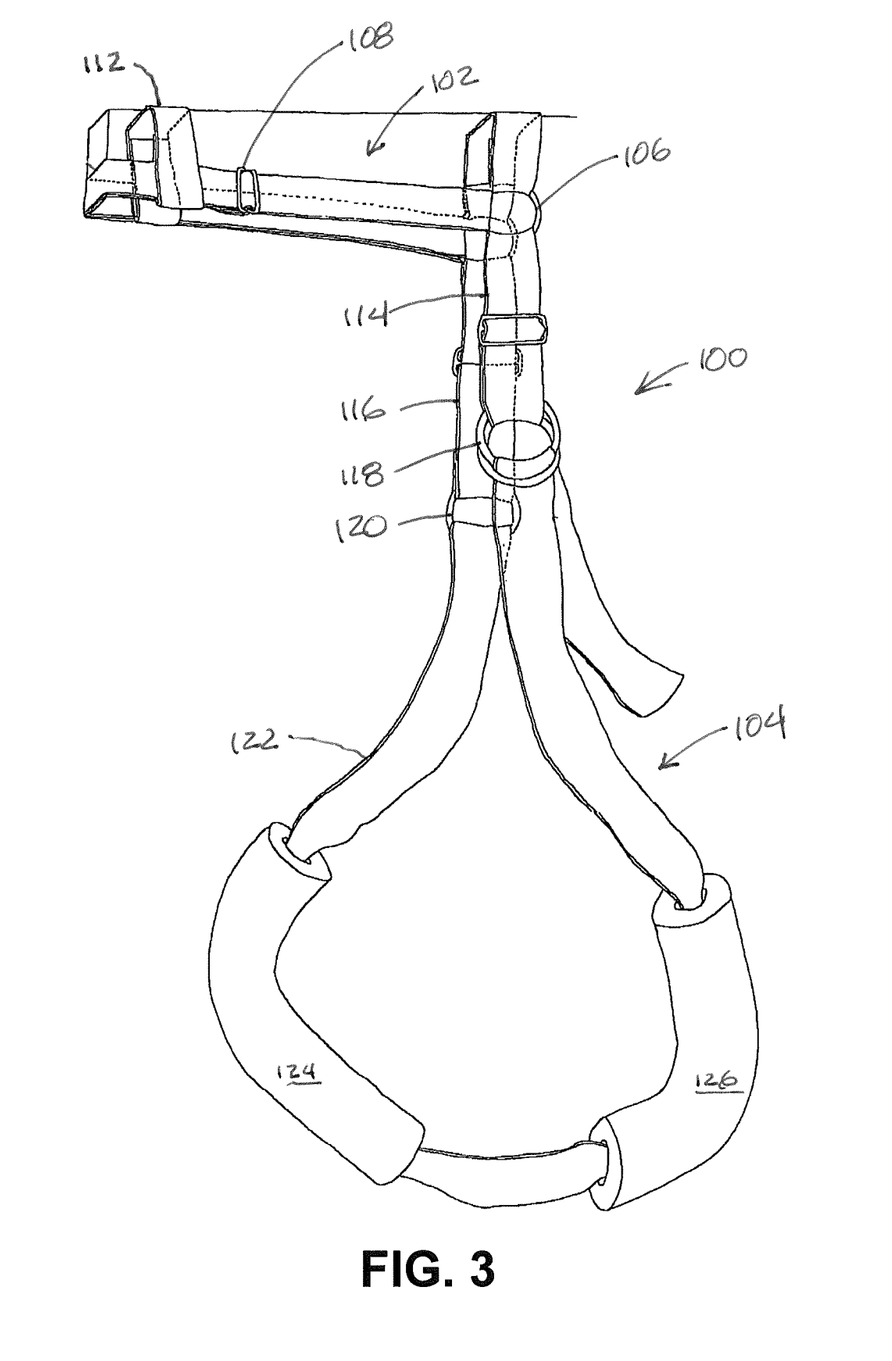
FIG. 3 presents a third orthogonal view of a detachable orthopedic sling according to an exemplary embodiment of the disclosure.

FIGS. 1, 2 and 3 present an apparatus 100 according to a first embodiment of the disclosure. An attachment strap portion 102 is permanently attached to a sling portion 104 by attachment rings 106. In other embodiments, the sling 104 may be detachably coupled to the strap 102 using a carabiner, a J-hook, an S-hook, or other suitable quick coupler. The strap portion 102 is placed over a top side of a door of a building. The sling portion 104 is placed around the back and under the arms of a person for therapeutic traction treatment of the spine.

The attachment strap portion is configured to engage three sides of a top portion of the door, as well as the top side of the door. The strap portion 102 includes a slide adjustment mechanism 108 to permit a length of the strap 102 to be changed to adapt to a width of the door 110. A hinge side of the strap 102 includes a safety loop 112 to prevent the strap 102 from slipping off the door while the person is suspended in the sling 104.

In other embodiments, the apparatus 100 may be adapted for use with tall doors, for example, doors over nine feet high. In such embodiments, a attachment strap portion 102 is attached using a carabiner to the attachment rings 106 and flipped up to fit over the top side of the door on the handle side of the door and adjusted with the slider 108 to adjust for height.

The sling 104 includes adjustable sections 114 and 116, on the left and right side, respectively, to allow for vertical positioning of handholds 118 and 120. The handholds 118 and 120 serve as handles for the user, to enable proper use and ease of use of the sling 104. Depending on the orthopedic position desired by the user, these handles allow the user to easily pull himself up to a standing vertical position and maneuver within the sling 104.

The sling 104 also includes a strap 122 that extends between the handholds 118 and 120. The handhold 120 is a single ring, and one end of the strap 122 is attached to the ring 120 by a loop in a first end of the strap 122. The handhold 118 is a pair of rings, and a second end of the strap 122 passes through the pair of rings. In this way, a length of the strap 122 may be adjusted to further adapt the sling 104 to the needs of the user. Pads 124 and 126 are slideably attached to the strap 122. The strap 122 is configured to permit a user to position the strap 122 around his torso, under his arms, and across his back, and to hang from the sling to provide traction treatment of the user's spine.

While the single ring of handhold 120 and the double ring of handhold 118 function both as handholds and as attachment points for the strap 122, in other embodiments separate structures may be used to serve as attachment points and handles. Such handles may include a T-shaped handle or other handle adapted for comfortable grasping by a user's hand.

Figure 9:
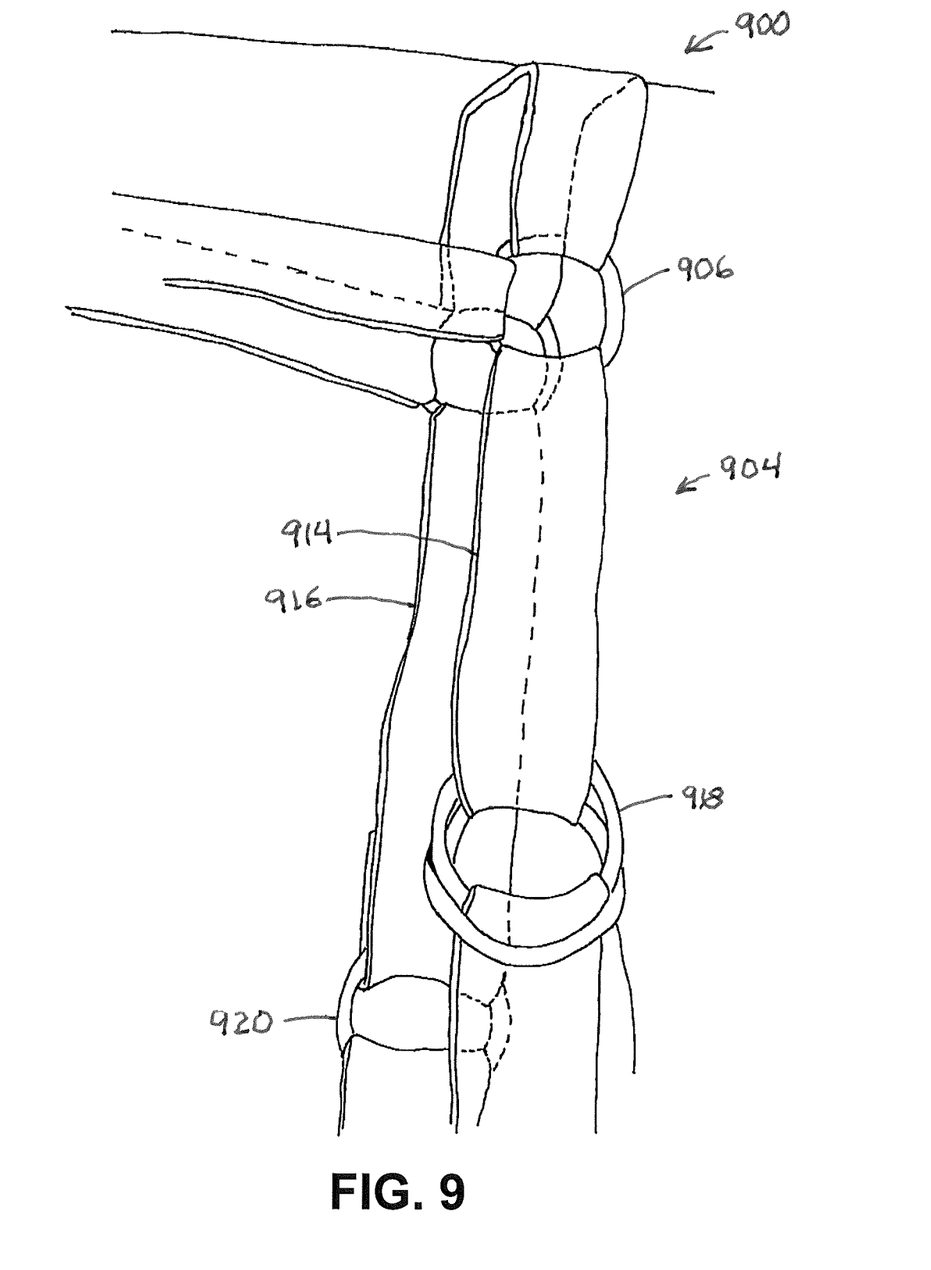
FIG. 9 presents an orthogonal view of a portion of an exemplary embodiment of the disclosure.

FIG. 9 shows a portion of an apparatus 900 according to another embodiment of the disclosure. A sling 904 includes non-adjustable sections 914 and 916, extending from attachment rings 906 to handholds 918 and 920, respectively. The sections 914 and 916 have loops at each end to couple to the attachment rings 906 and the handholds 918 and 920.

Figure 10:
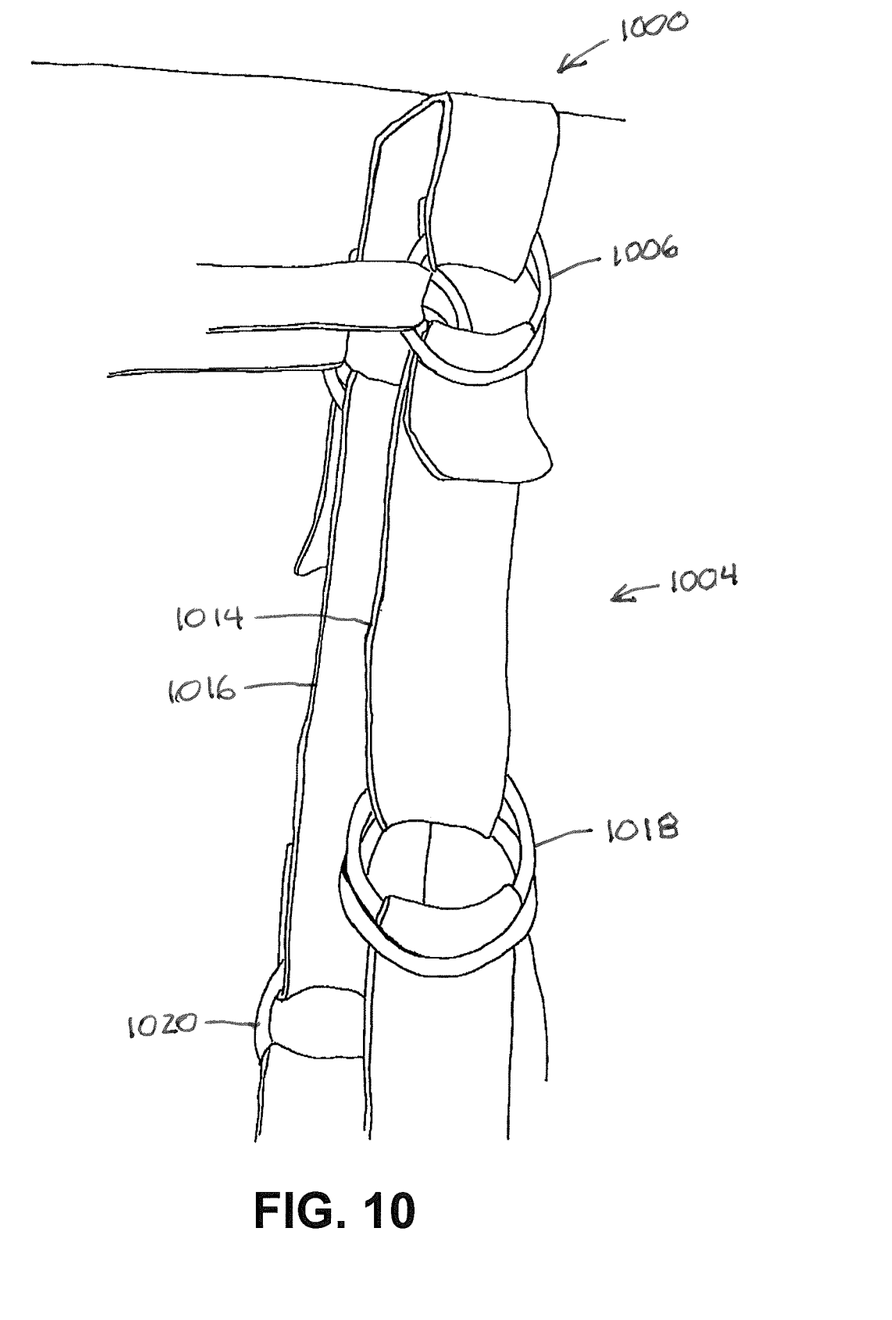
FIG. 10 presents an orthogonal view of a portion of another exemplary embodiment of the disclosure.

FIG. 10 shows a portion of an apparatus 1000 according to yet another embodiment of the disclosure. A sling 1004 includes adjustable sections 1014 and 1016. A loop at one end of the section 1014 couples the section 1014 to a handhold 1018. A loop at one end of the section 1016 couples the section 1016 to a handhold 1020.

Attachment rings 1006 include double rings on each side of the apparatus 1000. Second ends of sections 1014 and 1016 pass through the double rings of the attachment rings 1006 in a conventional cinch arrangement, to permit adjustment of the lengths of sections 1014 and 1016.

Figure 4:
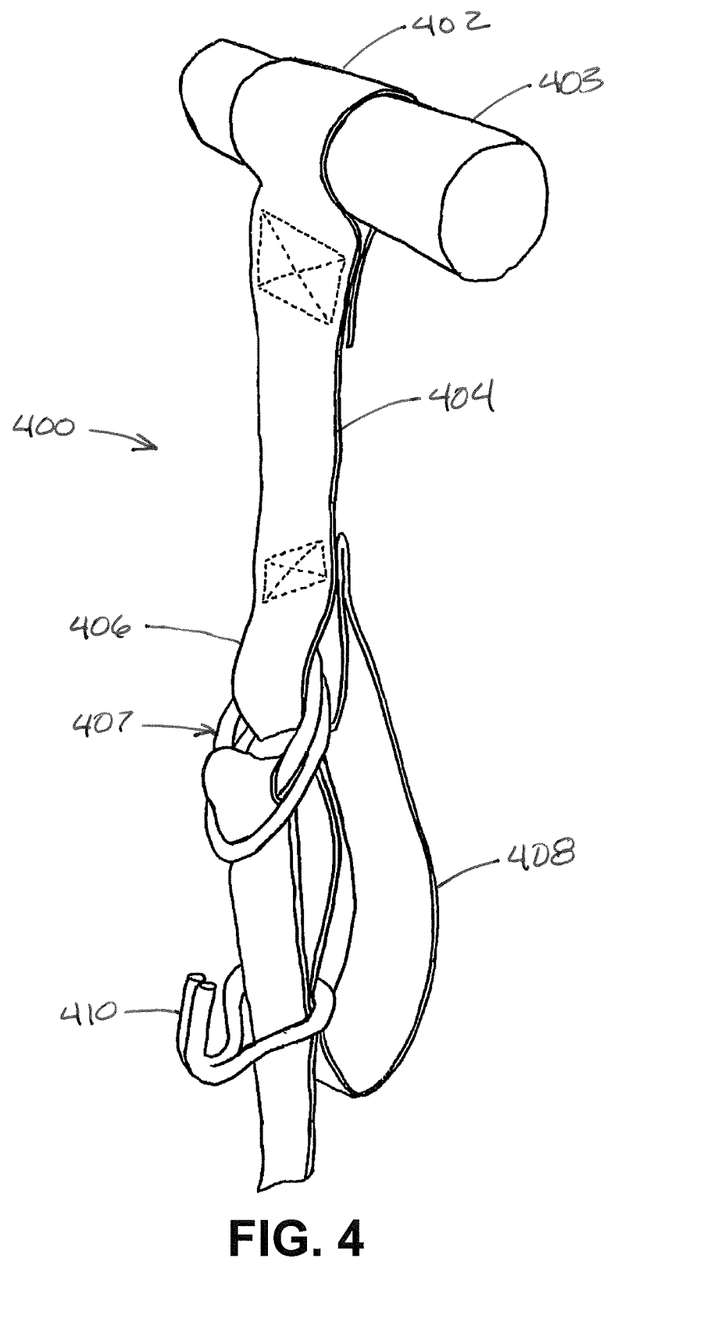
FIG. 4 illustrates an attachment strap according to another exemplary embodiment of the disclosure.

FIG. 4 shows an attachment strap 400 according to another embodiment of the disclosure. The strap 400 includes a first end having a loop 402, sized to accept a removable anchor 403. In this embodiment, the removable anchor 403 is a cylindrical wooden dowel. In other embodiments, it will be understood that the removable anchor 403 may have any suitable shape and be fabricated of any suitable material. In still other embodiments, an anchor may be formed from the material of the attachment strap 400, for example by forming a knot or by forming and securing a roll of the material.

Extending from the loop 402 is an extension portion 404 of the strap 400. The loop 402 and removable anchor 403 may be located in the interior of a car, truck or other vehicle and the extension portion 404 laid over a top side of a door of the vehicle. When the door is closed, the extension portion 404 passes between the top side of the door and a door frame of the vehicle. When the user then attaches the sling 104 to the attachment strap 400 and places his weight on the sling 104, the removable anchor 403 operates to hold the attachment strap 400 in place.

In other embodiments, the section 404 may be extended such that, after closing a first door of the vehicle to trap the anchor, the section 404 is passed over a top side of the vehicle to hang down on an opposite side of the vehicle from the first door. The user may then open a second door, on the opposite side of the vehicle, and place his legs partially within the interior of the vehicle while using the sling 104.

The attachment strap 400 further includes a loop 406 at an opposite end of the portion 404 from the loop 402. Permanently captured in the loop 406 are two rings 407, preferably having a diameter of 2 inches.

An adjustment portion 408 of the attachment strap 400 extends from the loop 406. The adjustment portion 408 is attached to a coupling mechanism 410. In the embodiment shown in FIG. 4, the coupling mechanism is a J-hook and the adjustment portion 408 passes through a base portion of the J-hook, threaded through the two rings 407, and back through the base portion of the J-hook. The rings 106 (or other quick couplers) of the sling 104 may be removably coupled to the coupling mechanism 410. The cinch mechanism formed by the adjustment portion 408 and the rings 407 may be used to adjust a distance of the coupling mechanism 410 from the removable anchor 403, thus adjusting a height of the coupling mechanism 410 from the ground, and thereby adjusting a height of the sling 104.

While the coupling mechanism 410 is depicted as a J-hook, it will be understood that any other suitable quick release mechanism may be used in other embodiments.

In an embodiment of the sling 104 used with the attachment strap 400, the two attachment rings 106 may be replaced with a single attachment ring, to which both adjustable sections 114 and 116 are coupled.

Figure 5:
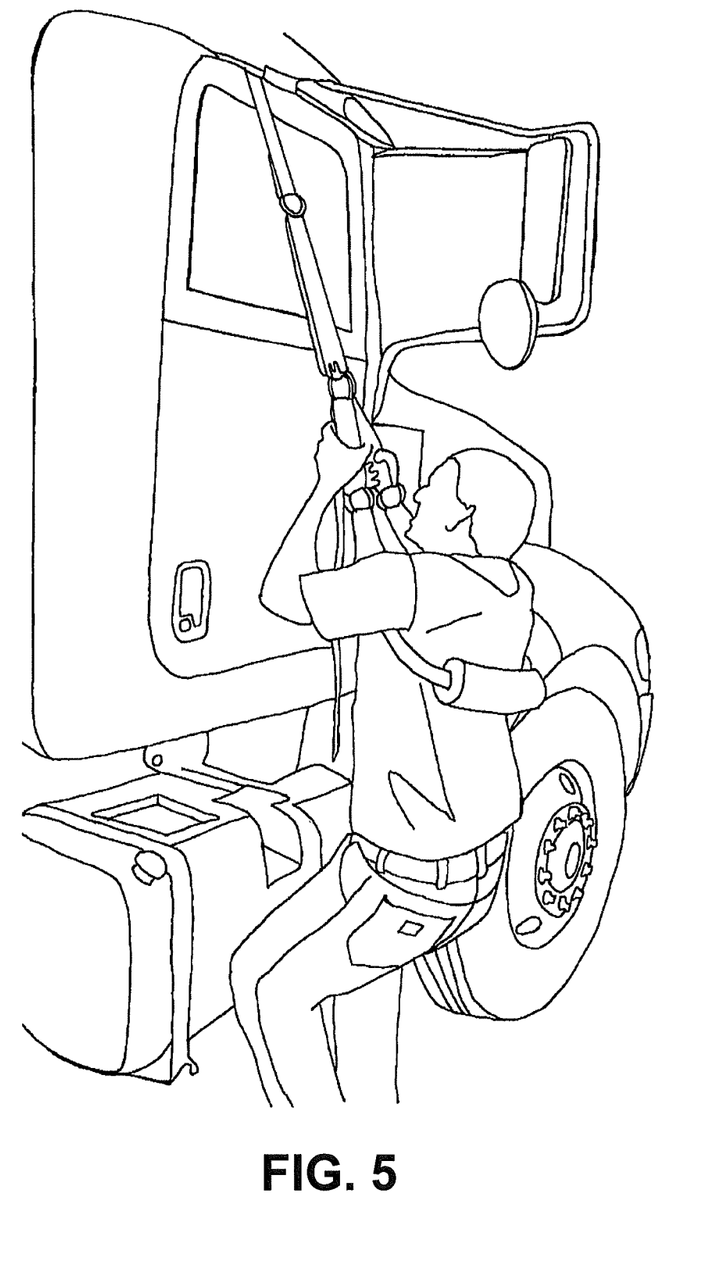
FIG. 5 presents an orthogonal view of an exemplary embodiment of the disclosure in use.
Figure 6:
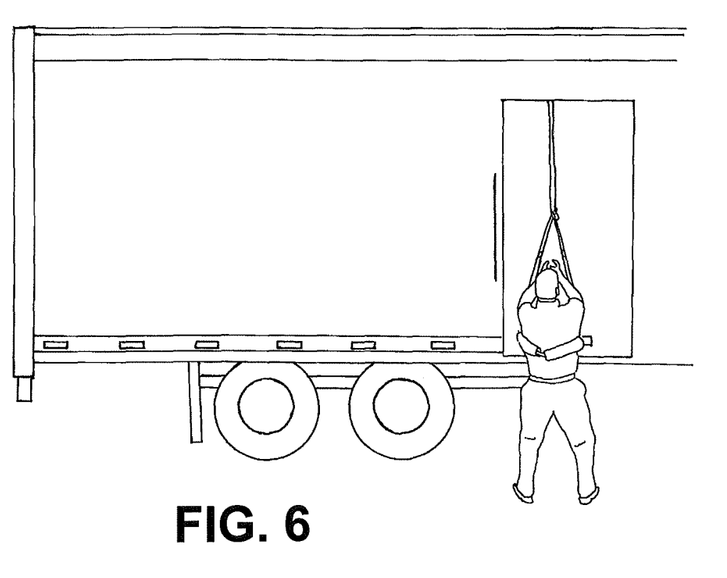
FIG. 6 presents an orthogonal view of an exemplary embodiment of the disclosure in use.

FIG. 5 depicts the attachment strap 400 and the sling 104 in use, attached to a door of a truck cab. FIG. 6 depicts the attachment strap 400 and the sling 104 in use, attached to a door of a truck trailer.

Figure 7:
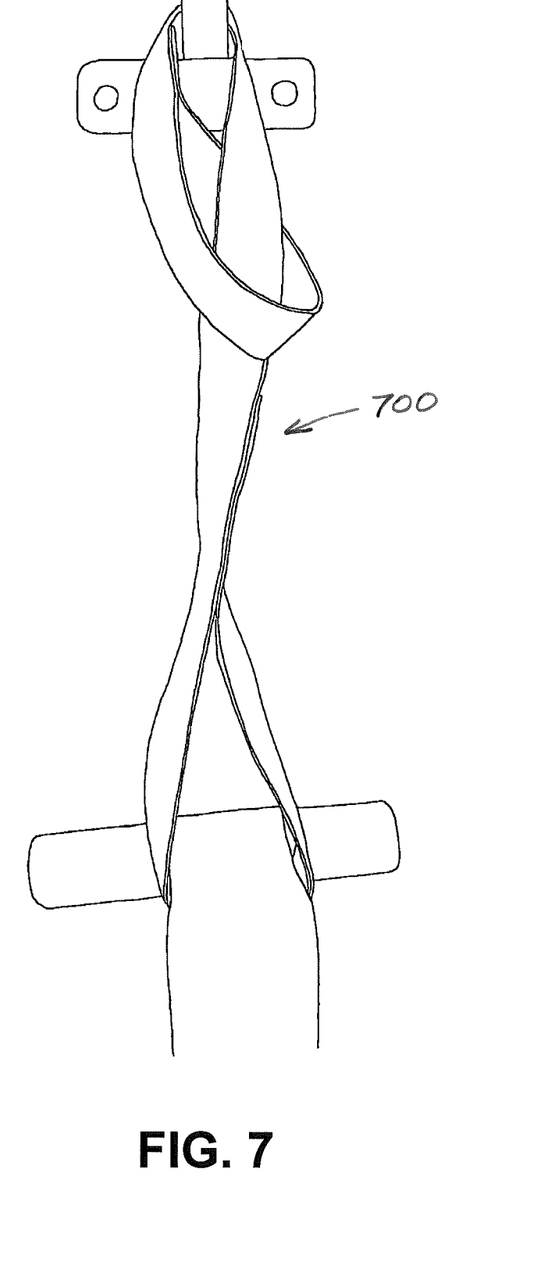
FIG. 7 illustrates an attachment strap according to yet another exemplary embodiment of the disclosure.

FIG. 7 shows an attachment strap 700 according to another embodiment of the disclosure. The attachment strap 700 may be used with the attachment strap 400 to support the sling 104 from any suitably sturdy support structure. The attachment strap 700 includes first and second attachment features at corresponding first and second ends of the strap 700. A first end of the strap 700 may be passed around the structure and the second end of the strap 700 passed through the first attachment feature, a loop material of the strap 700, to couple the strap 700 to the structure. The removable anchor 403 and loop 402 of the attachment strap 400 may be passed through the second attachment feature, a loop at the second end of the strap 700, to secure the strap 400 to the strap 700. In other embodiments, the attachment rings 106 may be coupled directly to one of the first and second attachment features of the strap 700 using any suitable quick release coupler.

Figure 8:
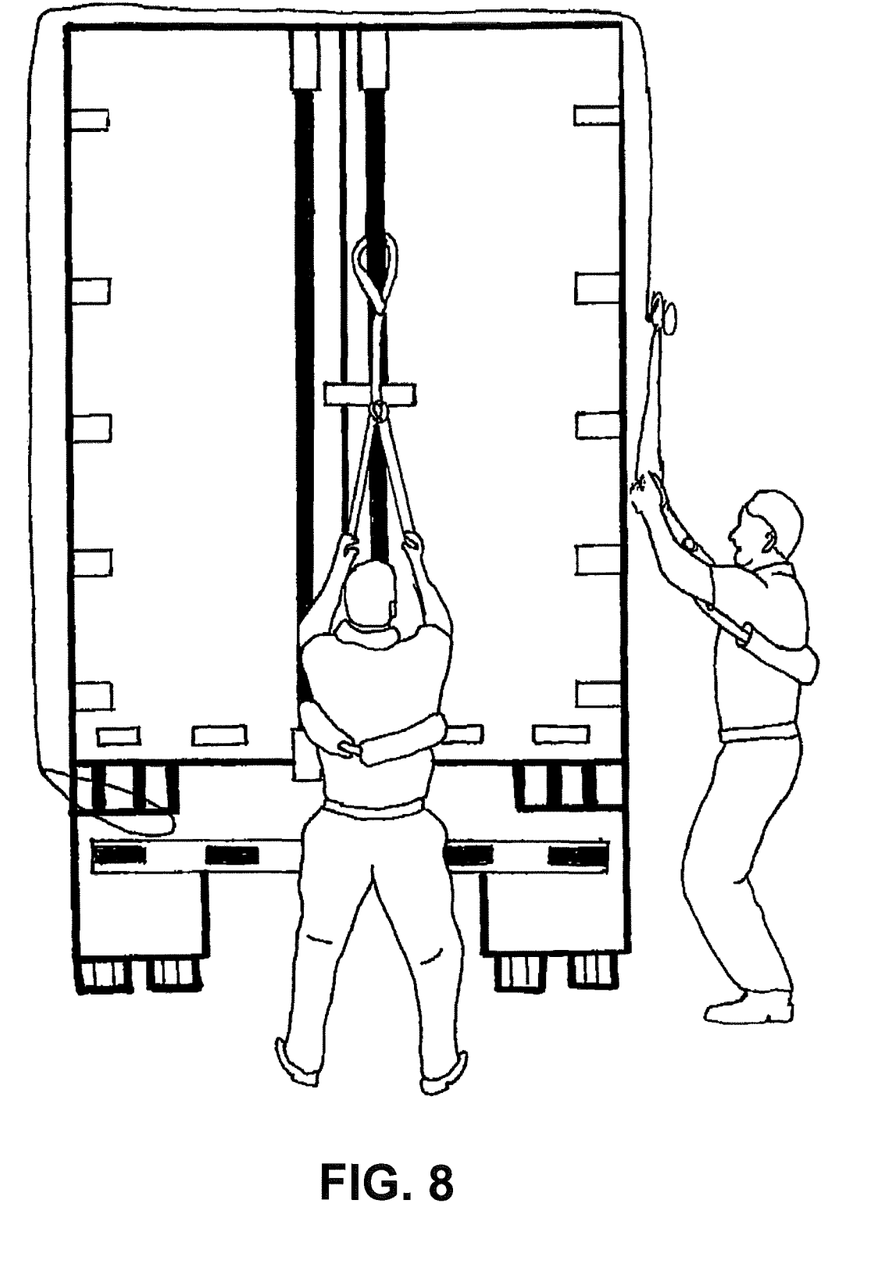
FIG. 8 presents an orthogonal view of two exemplary embodiments of the disclosure in use.

FIG. 8 shows the attachment strap 700, the attachment strap 400, and the sling 104 in a first configuration: attached to a vertical structure on a rear door of a truck trailer. FIG. 8 also shows an elongated embodiment of the attachment strap 700 in a second configuration: coupled to a structure under a first side of the truck trailer, passed over a top side of the truck trailer, and extending down a second side of the truck trailer (the second side is opposite the first side).

In the second configuration, other embodiments of the attachment strap 700 may include a J-hook, carabiner, or other suitable quick coupler, as the first attachment feature, configured to couple directly to a hole or other feature of a structure of the truck, or to be otherwise coupled to the structure without having to pass the entire length of the strap 700 through the loop in the first end of the strap 700. Still other embodiments of the attachment strap 700 may include a J-hook, carabiner, or other suitable quick coupler, as the first attachment feature, configured to couple to the attachment strap 400 or to the attachment rings 106.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A detachable orthopedic sling for treatment of a user's spine, comprising:
   first and second adjustable sections, wherein the first and second adjustable sections are configured to permit adjustment of their respective lengths;
   first and second handholds, wherein the first and second adjustable sections extend from one or more attachment rings to the first and second handholds, respectively; and
   a strap extending from the first handhold to the second handhold, wherein the strap is configured to permit adjustment of its length and to be positioned by a user around his torso, under his arms, and across his back,
   wherein the detachable orthopedic sling is configured to mechanically couple to a support structure using the one or more attachment rings and to allow the user to hang from the sling to provide traction treatment of the user's spine.

2. The detachable orthopedic sling of claim 1, wherein the first and second handholds comprise one or more rings that are configured to couple to the strap and to permit adjustment of the length of the strap.

3. The detachable orthopedic sling of claim 1, wherein the strap comprises one or more pads, slideably coupled to the strap.

4. The detachable orthopedic sling of claim 1, further comprising a first attachment section configured to detachably couple to the one or more attachment rings and to the support structure.

5. The detachable orthopedic sling of claim 4, wherein the first attachment section is configured to engage a top side of a door and three sides of a top portion of the door.

6. The detachable orthopedic sling of claim 5, wherein the first attachment section comprises an adjustment mechanism, configured to adjust the first attachment section according to a dimension of the door.

7. The detachable orthopedic sling of claim 4, wherein the first attachment section comprises:
   an anchor;
   an extension portion; and
   a coupling mechanism, adapted to couple to the attachment rings,
   wherein the first attachment section is configured to couple to a door by placing the extension section over a top side of the door and closing the door, such that the extension section passes between the top side of the door and a surrounding structure, with the anchor located on one side of the door and the coupling mechanism located on an opposite side of the door.

8. The detachable orthopedic sling of claim 7, wherein the anchor comprises a loop and a removable anchor.

9. The detachable orthopedic sling of claim 7, wherein the first attachment section further comprises an adjustment portion, adapted to adjust a distance of the coupling mechanism from the ground.

10. The detachable orthopedic sling of claim 4, further comprising a second attachment section including first attachment feature, configured to couple to a support structure, and a second attachment feature, configured to couple to the first attachment section.

11. A detachable orthopedic sling for treatment of a user's spine, comprising:
    a first attachment section, comprising first and second attachment rings;
    first and second adjustable sections, permanently coupled to the first and second attachment rings, respectively, wherein the first and second adjustable sections are configured to permit adjustment of their respective lengths;
    first and second handholds, wherein the first and second adjustable sections extend from the first and second attachment rings to the first and second handholds, respectively; and
    a strap extending from the first handhold to the second handhold, wherein the strap is configured to permit adjustment of its length and to be positioned by a user around his torso, under his arms, and across his back
    wherein the detachable orthopedic sling is configured to mechanically couple to a support structure using the one or more attachment rings and to allow the user to hang from the sling to provide traction treatment of the user's spine.

12. The detachable orthopedic sling of claim 11, wherein the first and second handholds comprise one or more rings that are configured to couple to the strap and to permit adjustment of the length of the strap.

13. The detachable orthopedic sling of claim 11, wherein the first and second handholds comprise handles adapted for comfortable grasping by a user's hand.

14. The detachable orthopedic sling of claim 11, wherein the strap comprises one or more pads, slideably coupled to the strap.

15. The detachable orthopedic sling of claim 14, wherein the first attachment section is configured to engage a top side of a door and three sides of a top portion of the door.

16. The detachable orthopedic sling of claim 15, wherein the first attachment section comprises an adjustment mechanism, configured to adjust the first attachment section according to a dimension of the door.

* * * * *